United States Patent
Fritz et al.

(10) Patent No.: US 10,031,046 B2
(45) Date of Patent: Jul. 24, 2018

(54) METHOD FOR DETECTING DEFECTS IN A PISTON FOR AN INTERNAL COMBUSTION ENGINE

(71) Applicant: Mahle International GmbH, Stuttgart (DE)

(72) Inventors: Michel Fritz, Weissensee/Thueringen (DE); Gerhard Mook, Magdeburg (DE); Ioannis Papadopoulos, Winnenden (DE); Holger Schnell, Vaihingen/Enz (DE)

(73) Assignee: Mahle International GmbH (DE)

( * ) Notice: Subject to any disclaimer, the term of this patent is extended or adjusted under 35 U.S.C. 154(b) by 157 days.

(21) Appl. No.: 15/048,383

(22) Filed: Feb. 19, 2016

(65) Prior Publication Data

US 2016/0245720 A1    Aug. 25, 2016

(30) Foreign Application Priority Data

Feb. 20, 2015   (DE) .................... 10 2015 203 119

(51) Int. Cl.
  G01M 15/06   (2006.01)
  G01N 27/90   (2006.01)
(52) U.S. Cl.
  CPC .......... *G01M 15/06* (2013.01); *G01N 27/902* (2013.01)
(58) Field of Classification Search
  CPC .............................. G01M 15/06; G01N 27/902
  USPC ....................................................... 324/240
  See application file for complete search history.

(56) References Cited

U.S. PATENT DOCUMENTS

| 3,109,139 A | 10/1963 | Branker |
| 5,298,858 A | 3/1994 | Harrison |
| 8,436,608 B2 * | 5/2013 | Sun .................... G01N 27/904 324/222 |

(Continued)

FOREIGN PATENT DOCUMENTS

| DE | 3750237 T2 | 12/1994 |
| DE | 102010038459 A1 | 2/2012 |

OTHER PUBLICATIONS

Criterion Ndt: "Case Study—Piston Flaw Testing Customer Problem", Jan. 1, 2014 (http://criterionndt.com/wp-content/uploads/2014/Eddy-Current-Piston-Flaw-Testing.pdf).

(Continued)

*Primary Examiner* — Manish S Shah
*Assistant Examiner* — Anthony W Megna Fuentes
(74) *Attorney, Agent, or Firm* — Fishman Stewart PLLC

(57) ABSTRACT

A method for detecting defects in a piston for an internal combustion engine may include providing the piston in a measurement arrangement that includes a measurement probe having a first electrical coil element for generating an electromagnetic alternating field and a second electrical coil element for detecting an electromagnetic alternating field. The method may also include moving the measurement probe over a piston surface of the piston, and providing an electrical alternating current in the first coil element to generate an electromagnetic alternating field that interacts with a material of the piston in the region under the piston surface. The method may further include evaluating an electrical alternating voltage induced in the second coil element by the electromagnetic alternating field after interaction with the material of the piston.

20 Claims, 3 Drawing Sheets

(56) References Cited

U.S. PATENT DOCUMENTS

| | | | |
|---|---|---|---|
| 8,803,516 B2 * | 8/2014 | Hibino | G01N 27/82 |
| | | | 324/225 |
| 2010/0207620 A1 | 8/2010 | Gies | |

OTHER PUBLICATIONS

European Search Report for European Patent Application No. 16155491.0, dated Jun. 23, 2016.
English abstract for DE-102010038459.
English abstract for DE-3750237.
Mook et al., "Electromagnetic Imaging Using Probe Arrays", Application of Contemporary Non-Destructive Testing in Engineering, Sep. 1-3, 2009, Ljubljana, Slovenia 349-366.
German Search Report for DE-102015203119.5, dated Jan. 15, 2016.

* cited by examiner

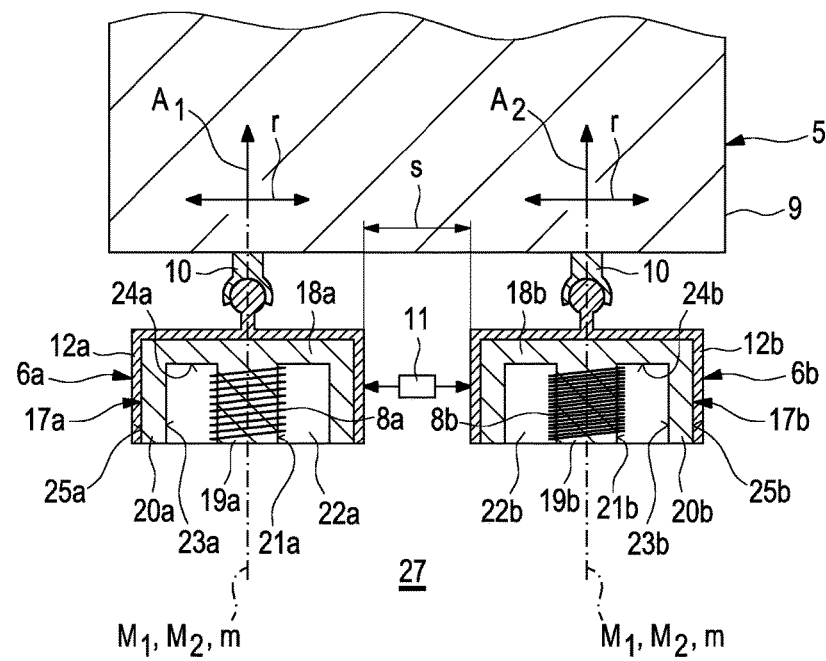
Fig. 3
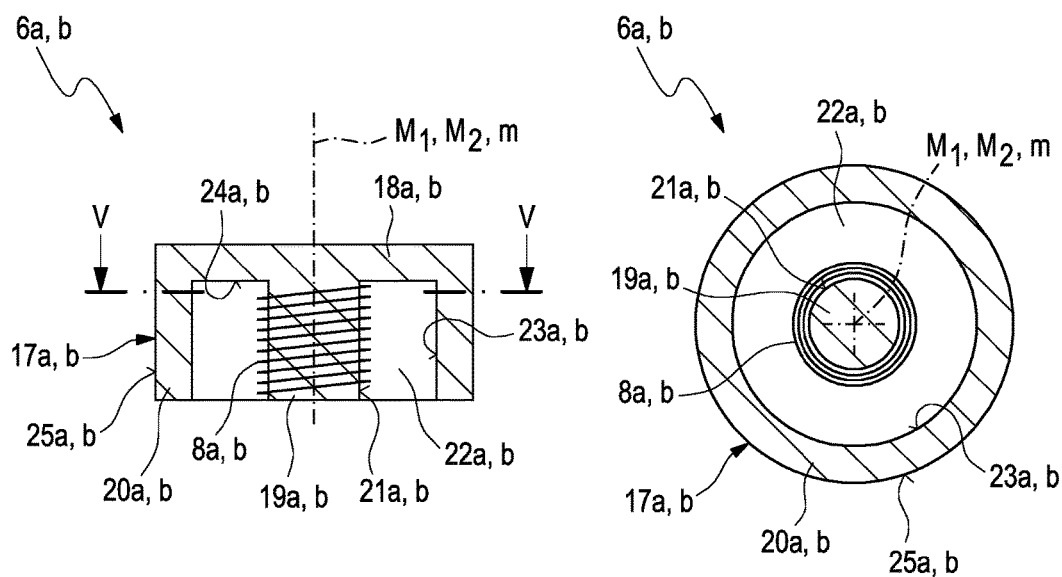
Fig. 4
Fig. 5

METHOD FOR DETECTING DEFECTS IN A PISTON FOR AN INTERNAL COMBUSTION ENGINE

CROSS-REFERENCE TO RELATED APPLICATIONS

This application claims priority to German Patent Application No. 10 2015 203 119.5, filed Feb. 20, 2015, the contents of which are hereby incorporated by reference in their entirety.

TECHNICAL FIELD

The invention relates to a method for detecting defects in a piston for an internal combustion engine. The invention also relates to a measurement arrangement for detecting defects in a piston for an internal combustion engine.

BACKGROUND

Pistons which are used as movable components in combustion chambers of internal combustion engines are subject to high mechanical and thermal loads. This makes it virtually imperatively necessary for said pistons to be produced without so-called defects which could considerably reduce both wear resistance and the service life of the piston. This applies in particular to defects which arise in the region of that piston region, known to a person skilled in the art as "piston depression", which axially delimits the combustion chamber of the internal combustion engine in the movement direction of the piston.

Here, in the present case, the expression "defects" is to be understood to mean any type of cracks, pores, fractures etc. in the material of the piston. Since such defects normally arise intrinsically, that is to say below the piston surface, within the piston, nondestructive detection—that is to say the detection of any defects present in the piston—is normally associated with cumbersome detection processes. Such conventional nondestructive testing methods are normally based on the use of eddy current sensors. Such sensors are based on the detection of an electromagnetic field generated with the aid of a coil which, for this purpose, has an electrical alternating current pass through it. Through interaction of the electromagnetic field with the material of the piston in the region of the piston surface, it is possible for defects that are not visible from the outside to be detected by virtue of the electromagnetic field being analyzed after its interaction with the piston material.

In the case of such conventional testing methods, it has proven to be disadvantageous that, typically, considerable disturbance influences are encountered, for example the lift-off effect between sensor and piston surface, complex aperture characteristics of the sensors, and only a small depth of penetration of the electromagnetic field into the piston surface, which impedes the detection specifically of defects with small dimensions. Furthermore, only the detection of open defects or defects in the immediate vicinity below the piston surface is ensured. By contrast, defects that have formed even a few tenths of a millimetre below the surface of the piston normally remain hidden to eddy current sensors. The grain structure of the piston microstructure often leads, in conjunction with the differentiating action of the differential probes used, to increased microstructure noise in the eddy current signal, which has an adverse effect on the defect detection sensitivity.

SUMMARY

It is therefore an object of the present invention to provide an improved nondestructive (testing) method which makes it possible, in particular, for defects in the piston being examined to be detected with increased accuracy. It is a further object of the invention to provide an improved (testing) arrangement for executing a method of said type.

Said objects are achieved by way of the subject matter of the independent patent claims. The dependent patent claims relate to preferred embodiments.

It is accordingly the basic concept of the invention to use a measurement probe with nondestructive action, in particular an eddy current measurement probe, for the examination of the piston material in a region close to the surface of the piston depression of the piston. Such a measurement probe comprises a first and a second coil element which, in the method proposed here, are part of a measurement arrangement in which the piston being examined can be received. As a result of electrical energization with an electrical alternating current, the first coil element generates an electromagnetic field which, with suitable positioning of the coil elements close to the surface of the piston, penetrates into said piston and interacts, within the piston, with the material of the piston. The method according to the invention utilizes the fact that said interaction is influenced by any defects that are present in the piston. Since a part of the electromagnetic field that has penetrated into the piston emerges from the piston again after interacting with the piston material, said electromagnetic field can be detected there by the second coil element. In the method proposed here, this is performed by evaluation of the electrical alternating voltage that is induced in the second coil element by the electromagnetic field in the second coil element. For this purpose, the second coil element may comprise a suitable evaluation device which, using a conventional voltage sensor, is capable of complex-value identification, and evaluation, of the electrical alternating voltage induced in the second coil element.

In order to be able to examine various regions of the piston with regard to the presence of defects, the measurement probe is, with a spacing, moved over the surface of the piston, in particular the depression surface of the piston depression, along a predetermined measurement path. During the movement, the first coil element is fed with an electrical alternating current and, in this way, an electromagnetic field which interacts with the material of the piston in the region below the depression surface is generated. Said electrical alternating current may in this case be generated by way of a suitable current source, which in turn may be activated by a control device, for example a conventional computer system. The movement of the measurement probe may be realized by way of a suitable electric drive unit. Here, the movement may be performed along a predefined measurement path which may run in a meandering or grid-like manner as seen in a plan view of the piston surface. Here, it is of major importance that the sampling path be defined such that all regions of the piston to be examined can be detected, without gaps, by the measurement probe.

The construction and mode of operation of the drive unit and of the receiving device for receiving a piston are not central to the invention discussed here, and therefore will not be discussed in any more detail below, especially as suitable setups are familiar to a person of relevant skill in the art in a variety of forms from conventional measurement setups, such as for example the abovementioned eddy current sensors.

In a preferred embodiment, for the execution of the method according to the invention, a first coil element is provided which has a first winding. The first winding may be a multi-layer cylindrical winding and may be arranged, without a support, on a central web of a shell-like ferrite core, also known to a person skilled in the art as "ferrite shell core" or "ferrite pot core". Such a ferrite shell core or pot core is known for example from the IEC standard 62317-2. Analogously to the first winding, for the execution of the method, a second coil element is provided which has a second winding. It is also possible for the second winding to be a multi-layer cylindrical winding and to be arranged, without a support, on a central web of a shell-like second ferrite core. The open face sides of the two shell-like ferrite cores point in the same direction toward the piston surface to be examined. Experimental tests have shown that the use of said shell cores reduces the sensitivity of the two coil elements to external electromagnetic disturbance signals, reduces the sensitivity of the measurement signal to fluctuations in the spacing between measurement probe and piston surface, and achieves a greater depth of detection for the defects. The proposed use of the shell cores in a semi-transmission arrangement —in each case adjacently arranged individual shells—thus consequently leads to improved detection sensitivity for defects.

The two coil elements are particularly expediently moved over the depression surface with a spacing to said depression surface, wherein said predetermined spacing is preferably at least 0.1 mm. The measurement probe used in the method according to the invention with two coil elements thus eliminates, for the detection of an electromagnetic field emerging from the piston, the need for the sensor arrangement that is used to be placed extremely close to the piston surface, such as would be necessary with the use of conventional eddy current sensors. This simplifies the structural design of the measurement arrangement considerably, which applies in particular to the movement mechanism for the movement of the measurement probe along the measurement path. Also, in this way, the risk of damage to the sensors as a result of undesired contact with the surface of the piston to be examined can be minimized.

In another preferred embodiment, the movement of the measurement probe is performed, using a suitable movement mechanism, along a predetermined measurement path. It is particularly preferable here for the predetermined sampling or measurement path to have a meandering form as seen in a plan view of the depression surface. In variants, differently selected measurement paths are also possible. Here, it is crucial that, regardless of the form of the sampling path selected, all surface regions of the piston that are to be examined are also covered by the measurement probe.

In an advantageous refinement of the invention, the spacing of the two coil elements to one another is varied during the execution of the method. Alternatively or in addition, it is also possible for a tilt angle of the two electrical coil elements relative to one another to be varied during the execution of the method. Through variation of the spacing between the coil elements, it is possible for the position and the sharpness of the so-called focus of the measurement probe, in the region of which the measurement probe has the greatest sensitivity with regard to the detection of defects, to be varied. The position of the focus in a direction perpendicular to the piston surface will particularly preferably vary, such that in this way, it is possible to identify defects in different depth regions below the surface of the piston. In the same way as through the variation of the spacing of the coil elements to one another as discussed above, the position and the sharpness of the focus of the measurement arrangement can also be varied by virtue of the two coil elements being tilted. With regard to the specific execution of the spacing variation and/or of the tilt variation, various configuration possibilities emerge to a person skilled in the art. For example, it is conceivable for the tilting or the spacing to be varied simultaneously with the movement of the measurement probe over the piston surface. As an alternative to this, it is possible for the measurement probe movement to be stopped during the spacing and/or tilt variation. Finally, provision may also be made for the movement of the piston over the piston surface to be repeated with different coil spacings and/or tilt angles. Finally, a parallel arrangement of multiple coil element pairs with in each case varied spacing to one another and/or tilt angle relative to one another, with different detection specification, is also conceivable.

The invention also relates to a measurement arrangement for detecting defects in a piston for an internal combustion engine, in particular for executing the method proposed above. Here, a measurement arrangement according to the invention comprises a receiving device in which the piston can be received for the execution of the defect detection. Here, the receiving device may be formed in the manner of a gripper, in which the piston to be examined is fixed, or may be realized as a sample table, on which the piston is arranged. With regard to the structural realization of the receiving device, a variety of options emerge to a person skilled in the art.

It is essential to the invention that, in the measurement arrangement, a measurement probe is provided which comprises a first and a second electrical coil element, arranged adjacent to the first coil element, for respectively generating and for detecting electromagnetic alternating fields. Here, the first coil element is arranged adjacent to the second coil element with a predetermined, in particular adjustable, coil spacing. With the aid of a suitable, preferably electrical, drive unit, the measurement probe of the measurement arrangement can, with a predetermined spacing, be moved over that surface of the piston which is to be examined with regard to defects when the piston is in a received state in the receiving device. Said movement is performed along a predetermined sampling or measurement path which may be stored in a control unit that interacts with the drive unit.

Said drive unit may be an electric drive unit, based for example on an electric motor, in particular an electric stepper motor, and may comprise a movement mechanism by means of which it is ensured that the selected spacing is adhered to during the movement along the measurement path, even if the piston surface has a non-planar surface contour in the region to be examined.

According to the invention, the first coil element comprises a first winding, which is provided on a first shell element of the first coil element. Analogously, the second coil element comprises a second winding, which is provided on a second shell element of the second coil element. As a result of electrical energization with an electrical alternating current, the first coil element generates an electromagnetic field which, when the coil elements are positioned close to the surface of the piston, penetrates into said piston and interacts, within the piston, with the material of the piston. Said interaction is influenced by defects present in the piston. That part of the electromagnetic field which has penetrated into the piston and which emerges out of the piston again after such interaction with the piston material can be detected there by the second coil element. Such an evaluation may for example be performed by analysis of the electrical alternating voltage that is induced in the second coil element by the electromagnetic field. For this purpose, the second coil element may cooperate with a suitable evaluation device which, using a conventional voltage sensor, is capable of complex-value detection, and evaluation, of the electrical alternating voltage induced in the second coil element.

In order to be able to examine various regions of the piston with regard to the presence of defects, the measurement probe can, with a spacing, be moved over the surface of the piston, in particular the depression surface of the piston depression, along a predetermined measurement path. During the movement, the first coil element is fed with the abovementioned first electrical alternating current and, in this way, an electromagnetic field which interacts with the material of the piston in the region below the depression surface is generated. The electrical alternating current may in this case be generated by way of a suitable current source, which in turn is activated by a control device, for example a conventional computer system. The movement of the measurement probe may be realized by way of a suitable, for example electric drive unit. Here, the movement may be performed along a predefined measurement path which may run in a meandering or grid-like manner as seen in a plan view of the piston surface. Here, it is of major importance that the sampling path be defined such that all regions of the piston to be examined are covered, without gaps, by the "field of view" of the measurement probe.

Also essential to the invention is the use of in each case shell-shaped or pot-shaped ferrite cores, or core arrangements of similar geometry, for example ferrite cylindrical cores with an additional coaxially surrounding ferrite sleeve, or ferrite E cores in the two coil elements of the measurement arrangement. Owing to the magnetic shielding action of the ferrite core arrangements, the sensitivity of the two coil elements with respect to external electromagnetic disturbance fields can be significantly reduced. At the same time, in the construction of the measurement arrangement, the focus of the electromagnetic field that interacts with the piston to be examined can be configured such that the influence of changes in the spacing is minimized for a particular nominal spacing, and/or the interaction depth of the electromagnetic field into the piston material increases. It is thus possible to detect defects in regions deeper below the piston surface than would be possible with conventional eddy current sensors. The measurement arrangement according to the invention permits the detection of defects with very small dimensions, in particular of defects which have a diameter of less than 0.3 mm.

It is particularly expediently possible for the first winding, in the form of a multi-layer cylindrical winding, to extend along a first axial direction and for the second winding, likewise in the form of a multi-layer cylindrical winding, to extend along a second axial direction. In this embodiment, the two coil elements are arranged so as to be adjacent to one another and tilted relative to one another, such that the axial first direction forms a predetermined tilt angle with the second axial direction.

The tilt angle may particularly preferably be an acute angle, which preferably lies between 0° and 45°.

It is particularly expediently possible for the coil elements to be received, in particular releasably, in a respective holding element. In this variant, the two holding elements are designed to be linearly adjustable relative to one another and/or tiltable relative to one another, preferably by way of a tilting and/or adjustment device. This makes it possible in a simple manner for the spacing between the coil elements, and/or the tilt angle thereof relative to one another, to be varied. In this way, the position and characteristics of the focal point of the measurement probe can be set particularly accurately.

In a particularly preferred embodiment, which can be realized with particularly little outlay in terms of construction, the two holding elements are attached in linearly adjustable fashion to a common main body of the measurement probe.

In another preferred embodiment, each of the two coil elements comprises a shell element with a base part of cylindrical form. A first cylindrical ferrite core element projects from the base part, the central longitudinal axis of which first ferrite core element runs coaxially with respect to the central longitudinal axis of the base part and on the outer circumferential surface of which first ferrite core element the respective winding is arranged. Furthermore, a hollow cylindrical second ferrite core element also projects from the cylindrical base part, which second ferrite core element is consequently of ring-shaped form in a cross section transversely with respect to the central longitudinal axis. The central longitudinal axis of the second ferrite core element likewise runs coaxially with respect to the central longitudinal axis of the base part and is arranged radially outside the first ferrite core element, such that an intermediate space is formed between the first and the second ferrite core element. Said intermediate space is thus delimited, in a radial direction, radially at the inside by the outer circumferential surface of the first ferrite core element and radially at the outside by the inner circumferential surface of the second ferrite core element. At the face side, the intermediate space is delimited by the base part. By contrast, opposite the face side, the intermediate space is open.

Further important features and advantages of the invention will emerge from the subclaims, from the drawing and from the associated description of figures on the basis of the drawing.

It is self-evident that the features mentioned above and the features yet to be discussed below may be used not only in the respectively specified combination but also in other combinations or individually without departing from the scope of the present invention.

Preferred exemplary embodiments of the invention are illustrated in the drawing and will be discussed in more detail in the following description, wherein the same reference signs are used to denote identical or similar or functionally identical components.

BRIEF DESCRIPTION OF THE DRAWINGS

In the drawing, in each case schematically:

FIG. 3 is a sectional detail illustration of the measurement probe of FIG. 2 in the region of the electrical coil elements of the measurement probe, FIG. 4 is a detail illustration of one of the two electrical coil elements of FIG. 3, FIG. 5 shows the coil element of FIG. 4 in a cross section along the section line V-V of FIG. 4.

DETAILED DESCRIPTION

Figure 1:
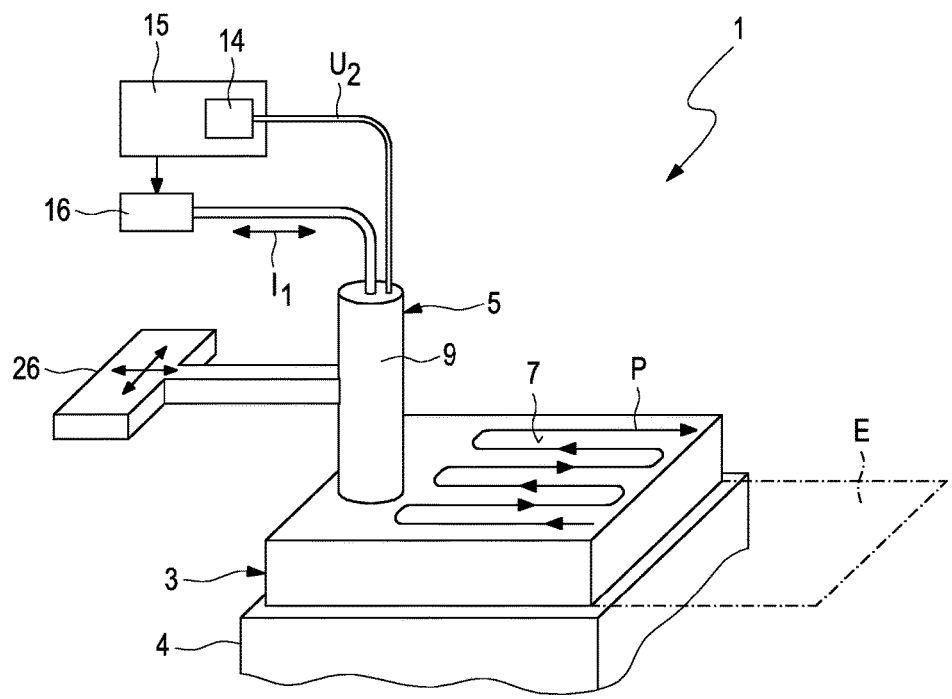
FIG. 1 shows an example of a measurement arrangement according to the invention for determining defects in a piston for a motor vehicle.

FIG. 1 shows, in a schematic illustration, an example of a measurement arrangement 1 according to the invention for detecting defects 2 in a piston 3—illustrated merely in highly schematic form in FIG. 1—for an internal combustion engine. The measurement arrangement 1 is suitable in particular for executing the method according to the invention as discussed above. The measurement arrangement 1 comprises a receiving device 4 for receiving the piston 3. Said receiving device may be formed in the manner of a gripping device or, as indicated in highly schematic form in FIG. 1, in the manner of a sample table. The measurement arrangement 1 furthermore comprises a measurement probe 5, which is likewise depicted merely highly schematically in FIG. 1 and which in turn has a first and a second coil element 6a, 6b for the generation and detection of an electromagnetic alternating field.

Figure 2:
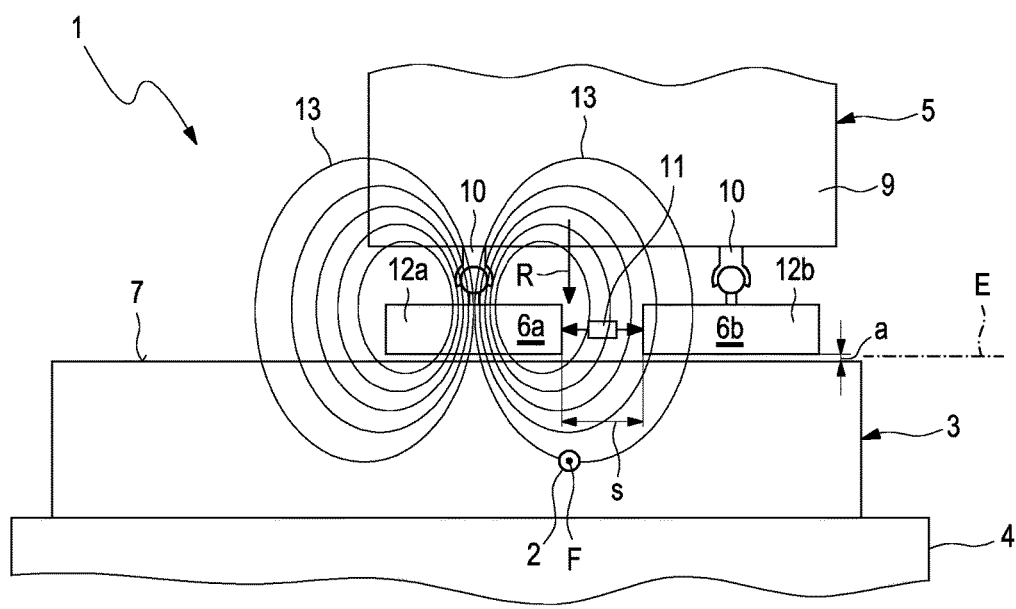
FIG. 2 is a detail illustration of the measurement arrangement of FIG. 1 in the region between a measurement probe of the measurement arrangement and the piston surface of the piston to be examined.

FIG. 2 shows the measurement arrangement 1 in the region of the measurement probe 5. It can be seen that the first coil element 6a is arranged with a predetermined coil spacing s to the second coil element 6b laterally, that is to say in a measurement plane E that is parallel to the piston surface 7. Here, the measurement probe 5 can, with a predetermined spacing a to the piston surface of the piston, be moved over the piston surface 7 along a predetermined measurement path P—schematically depicted in FIG. 1—by way of a drive unit 26. The exact structural design of the drive unit 26 is not the central subject of the invention proposed here, such that more detailed explanations will be omitted; a person skilled in the art is familiar with a variety of embodiments from which he can choose on the basis of practical considerations. In particular, an arrangement of scanner-like construction is conceivable, in conjunction with one or more electric stepper motors for moving the measurement probe 5 relative to the piston 3 along the measurement path P.

FIG. 3 illustrates the construction of the measurement probe 5 in a detail illustration in the region of the two coil elements 6a, 6b. Corresponding to FIG. 3, the first coil element 6a has a winding 8a which is arranged on a first shell element 17a, which is of shell-like form, of the first coil element 6a. Correspondingly, the second coil element 6b has a second winding 8b which, analogously to the first coil element 6a, is arranged on a second shell element 17b, which is of shell-like form, of the second coil element 6b. The first winding 8a may have, for example, twenty windings in order to provide an inductivity of 2.5 µH. The first winding 8b may have approximately 240 windings in order to provide an inductivity of 250 µH.

As a result of electrical energization with an electrical alternating current $I_1$, the first coil element 6a generates an electromagnetic field 13 which penetrates through the piston surface 7 into the interior of the piston 3 and interacts, within the piston 7, with the piston material. Said interaction is influenced by the defect 2, if such a defect is present. The electrical alternating current $I_1$ may in this case be generated by way of a suitable controllable electrical current source 16, which is then activated by a control device 15, for example a conventional computer system (cf. FIG. 1). The electrical alternating current $I_1$ may for example have a maximum amplitude of 100 mA at a frequency of between 50 and 200 kHz.

That part of the electromagnetic field 13 which emerges from the piston 3 again after interacting with the piston material is detected by the second coil element 6b by virtue of an electrical alternating voltage $U_2$ being induced in said coil element 6b and evaluated. For this purpose, the second coil element 6b may interact with a suitable evaluation device 14 in the form of a computer system which, for example, performs complex-value detection of the electrical alternating voltage $U_2$. Here, it is clear to a person skilled in the art that the control device 15 for controlling the electrical current source 16 and the evaluation device 14 may be integrated into one another.

In order to be able to examine different regions of the piston 3 with regard to the presence of defects 2, the measurement probe 5 is, with a spacing a, moved over the piston surface 7 of the piston 3, in particular the depression surface of the piston depression (not shown), along a predetermined measurement path P. During the movement, the first coil element 6a is fed with the electrical alternating current $I_1$, which generates the electromagnetic field 13 which interacts with the material of the piston 3 in the region below the piston surface 7. The movement of the measurement probe 5 is realized by way of the abovementioned drive unit 26. The movement of the measurement probe 5 is performed along the measurement path P, which runs in a meandering (cf. FIG. 1) or grid-like (not shown) manner as seen in the plan view of the piston surface 7. Other measurement path geometries are also conceivable in variants. In all of said variants, the measurement path P is preferably defined such that all regions of the piston 3 to be examined are covered by the "measurement field" of the measurement probe 5.

As can also be seen from FIG. 3, the two coil elements 6a, 6b are in the form of separate components. Each coil element 6a, 6b is received in a respective holding element 12a, 12b. The two holding elements 12a, 12b are designed to be linearly adjustable relative to one another and/or tiltable relative to one another. This is realized by way of an adjustment and/or tilting device 11, which is merely schematically indicated in FIG. 3 and which connects the two holding elements 12a, 12b to one another. In this way, the spacing s between the coil elements 6a, 6b, and the tilt angle α thereof relative to one another, can be varied.

Through variation of the coil spacing s, it is possible to vary the position of the focus of the measurement probe 5—schematically indicated and denoted by F in FIG. 2—in a direction R perpendicular to the piston surface 7, in the region of which focus the measurement probe has the greatest sensitivity with regard to the detection of defects. In this way, it is possible to detect defects in different depth regions below the piston surface 7 of the piston 3. Analogously to the variation of the spacing s, the position of the focus F in the direction R perpendicular to the piston surface 7 can also be varied by tilting of the two coil elements 6a, 6b relative to one another.

It is additionally possible for the two holding elements 12a, 12b to be attached in linearly adjustable fashion to a main body 9 of the measurement probe 5. This may be realized by way of a carriage 10. This makes it possible for the holding elements 12a, 12b to be adjusted transversely with respect to the main body 9. Such a transverse movement may be necessary because the piston depression, which is to be examined, of the piston 3 has an undercut. Holding elements 12a, 12b may be detachably fastened to the main body 9. A detachable fastening of the two coil elements 6a, 6b to one another and/or to the main body 9 facilitates the assembly of the measurement arrangement 1 if the spatially only poorly accessible region of a piston depression of the piston 3 to be examined is to be examined with regard to defects.

Correspondingly to FIG. 3, the first winding 8a extends in cylindrical form along a first axial direction $A_1$. Analogously, the second winding 8b extends in cylindrical form along a second axial direction $A_2$. As can be seen in FIG. 3, the two coil elements 6a, 6b are arranged adjacent to one another in the lateral measurement plane E and are parallel to one another with regard to the two directions $A_1$, $A_2$, that is to say are not tilted relative to one another.

In a direction transverse to the axial direction $A_1$, $A_2$, the coil elements 6a, 6b have a diameter of approximately 2.5 mm. The measurement probe 5 as a whole may have a diameter of approximately 90 mm in said direction. The dimensions of the holding elements 12a, 12b may be for example 35×30×20 mm.

Figure 6:
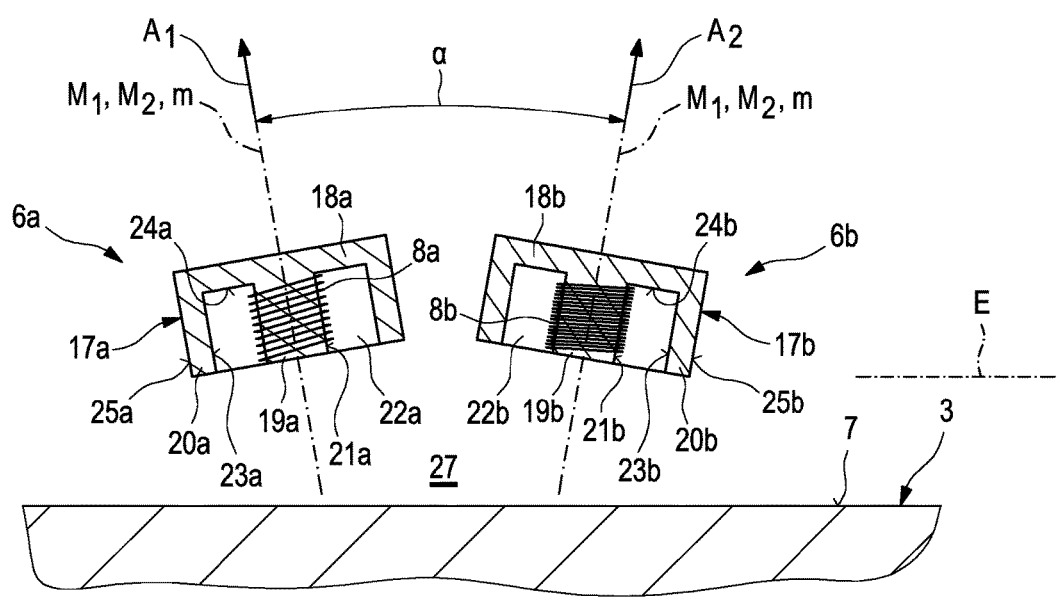
FIG. 6 shows a variant of the example of FIG. 3 with electrical coil elements tilted relative to one another.

FIG. 6 shows a variant of the example of FIG. 3 in which the two coil elements 6a, 6b (shown without the tilting/adjustment device 11 in FIG. 6) are arranged adjacently with respect to the lateral measurement plane E, analogously to the example of FIG. 3, and are arranged so as to be tilted relative to one another with regard to the two axial directions $A_1$, $A_2$. In other words, the first axial direction $A_1$ forms a predetermined tilt angle α with the second axial direction $A_2$. Here, the tilt angle α may, as shown in FIG. 6, be an acute angle, which may preferably lie between 0° and 45°. The tilting/adjustment device 11 may be designed such that the coil spacing s and/or the tilt angle α can be varied during the execution of the method according to the invention. It is for example conceivable for the coil spacing a and/or the tilt angle α to be varied during the course of the movement of the measurement probe 5 of the piston surface 7, in order to thereby vary the depth of penetration of the electromagnetic radiation generated by the first coil element 6a. In this way, it is possible to examine defects in different depth regions below the piston surface 7. If the depth of penetration of the measurement point of the electromagnetic radiation is to be varied, it is also conceivable for the movement of the measurement probe 5 to be temporarily stopped during such a variation. A variety of options for correspondingly varying the measurement process emerge to a person skilled in the art.

Considering FIG. 3 again, it can be seen that each of the two coil elements 6a, 6b has in each case one shell element 17a, 17b—also known to a person skilled in the art as ferrite shell core—with a base part 18a, 18b of cylindrical form, from which there projects a central web, hereinafter referred to as first cylindrical ferrite element 19a, 19b. The opening of the individual cells points in the direction of the piston surface 7 to be examined. The shell elements 17a, 17b may each have an initial permeability $\mu_i$ of approximately 450.

For illustrative purposes, FIG. 4 shows the electrical coil elements 6a, 6b separately and in an enlarged illustration. FIG. 5 shows the construction of the coil element 6a, 6b of FIG. 4 in a cross section along the section line V-V of FIG. 4.

As shown in FIGS. 3 to 5, the central longitudinal axis $M_1$ of the first ferrite core element 19a runs coaxially with respect to the central longitudinal axis m of the base part 18a, 18b. The first and second windings 8a, 8b, which are preferably of multi-layer form, are respectively arranged, without a support, on the outer circumferential surface 21a, 21b of the first ferrite core element 19a, 19b. Analogously to the first ferrite core element 19a, 19b, there also projects from the cylindrical base part 18a, 18b a hollow cylindrical second ferrite core element 20a, 20b, which is of ring-shaped form in a cross section transversely with respect to its central longitudinal axis $M_2$. The central longitudinal axis $M_2$ of the first ferrite core element 20a, 20b runs coaxially with respect to the central longitudinal axis m of the base part 18a, 18b. The second ferrite core element 20a, 20b is arranged radially outside the first ferrite core element 19a, 19b, such that an intermediate space 22a, 22b is formed between the first and the second ferrite core element 19a, 20a. The intermediate space 22a, 22b is, in a radial direction r, delimited radially at the inside by the outer circumferential surface 21a, 21b of the first ferrite core element 19a, 19b and radially at the outside by an inner circumferential surface 23a, 23b of the second ferrite core element 20a, 20b. At the face side, the intermediate space 22a, 22b is delimited by a face side 24a, 24b formed by the base part 18a, 18b. Opposite the face side 24a, 24b, the intermediate space 22a, 22b is open to the surroundings 27 of the coil elements 6a, 6b, specifically in the direction of the piston surface 7 to be examined.

Particularly good results in terms of the defect detection can be achieved if the first shell element 17a of the first electrical coil element 6a is of gapless form and, alternatively or in addition, the second shell element 17b of the first electrical coil element 6b is of gapless form. A particularly high level of detection sensitivity can also be achieved by virtue of the two coil elements 6a, 6b being arranged relative to one another such that an outer circumferential surface 25a of the second ferrite core element 20a of the first coil element 6a is situated opposite an outer circumferential surface 25b of the second ferrite core element 20b of the second coil element 6b.

The two ferrite core elements 19a, 19b, 20a, 20b may be formed integrally on the respective base part 18a, 18b by mechanical grinding. This provides an additional possibility for one-off fine adjustment of the position and sharpness of the focus of the measurement probe.

The invention claimed is:

1. A method comprising: providing a piston in a measurement arrangement that includes a measurement probe with a first electrical coil element for generating an electromagnetic alternating field and a second electrical coil element for detecting an electromagnetic alternating field, moving the measurement probe over a piston surface of the piston, providing an electrical alternating current in the first coil element to generate an electromagnetic alternating field that interacts with a material of the piston in the region under the piston surface, evaluating an electrical alternating voltage induced in the second coil element by the electromagnetic alternating field after interaction with the material of the piston, and varying a tilt angle of the two electrical coil elements relative to one another during movement of the measurement probe over the piston surface.

2. The method according to claim 1, wherein: the first coil element has a first winding arranged on a first shell element of the first coil element, and the second coil element has a second winding arranged on a second shell element of the second coil element.

3. The method according to claim 2, wherein the two coil elements are moved over the piston surface with a spacing to said piston surface.

4. The method according to claim 3, wherein the spacing is at least 0.1 mm.

5. The method according to claim 1, wherein the two coil elements are moved over the piston surface with a spacing to said piston surface.

6. The method according to claim 5, further comprising: varying a coil spacing between the two electrical coil elements.

7. The method according to claim 5, wherein moving the measurement probe is performed along a predetermined measurement path.

8. The method according to claim 7, wherein the measurement path is a meandering path along the piston surface.

9. The method according to claim 1, further comprising: varying a coil spacing between the two electrical coil elements.

10. The method according to claim 9, wherein the predetermined tilt angle is an acute angle.

11. The method according to claim 1, wherein moving the measurement probe is performed along a predetermined measurement path.

12. A measurement arrangement for detecting defects in a piston for an internal combustion engine, comprising:
a receiving device in which the piston is receivable,
a measurement probe having a first electrical coil element for generating an electromagnetic alternating field and a second electrical coil element for detecting a resultant electromagnetic alternating field after interaction with the piston, wherein the first coil element is arranged adjacent to the second coil element with a predetermined spacing therebetween and at a predetermined tilt angle relative to one another, and
a drive unit configured to move the measurement probe over a piston surface, with a spacing therebetween, along a predetermined measurement path when the piston is in a received state in the receiving device,
wherein the first electrical coil element has a first winding arranged on a first shell element of the first electrical coil element,
wherein the second electrical coil element has a second winding arranged on a second shell element of the second electrical coil element, and
wherein each of the two coil elements is releasably received in a respective holding element, and the two holding elements are at least tiltable relative to one another to vary at least the tilt angle.

13. The measurement arrangement according to claim 12, wherein: the first winding extends cylindrically along a first axial direction and the second winding extends cylindrically along a second axial direction, and the first axial direction is arranged at the predetermined tilt angle relative to the second axial direction.

14. The measurement arrangement according to claim 13, wherein: the two holding elements are linearly adjustable relative to one another to vary the spacing.

15. The measurement arrangement according to claim 14, wherein the two holding elements are linearly and adjustably attached to a common main body of the measurement probe.

16. The measurement arrangement according to claim 12, wherein the predetermined tilt angle is an acute angle.

17. The measurement arrangement according to claim 16, wherein the predetermined tilt angle is between 00 and 45°.

18. The measurement arrangement according to claim 12, wherein: the two holding elements are linearly adjustable relative to one another to vary spacing.

19. The measurement arrangement according to claim 18, wherein the two holding elements are linearly and adjustably attached to a common main body of the measurement probe.

20. The measurement arrangement according claim 6, wherein each of the two coil elements includes: a shell element with a cylindrical base part from which a first cylindrical ferrite core element project, a central longitudinal axis of the first ferrite core element running coaxially with respect to a central longitudinal axis of the cylindrical base part, and one of the first winding or the second winding being arranged on an outer circumferential surface of the first ferrite core element, a hollow cylindrical second ferrite core element projecting from the cylindrical base part, the hollow cylindrical second ferrite core element being of ring-shaped form in a cross section transvers to the central longitudinal axis of the cylindrical base part, a central longitudinal axis of the second ferrite core element running coaxially with respect to the central longitudinal axis of the cylindrical base part, the second ferrite core element being arranged radially outside the first ferrite core element such that an intermediate space is formed between the first ferrite core element and the second ferrite core element.

* * * * *